USO05637473A

United States Patent [19]
Clemmons

[11] Patent Number: 5,637,473
[45] Date of Patent: Jun. 10, 1997

[54] LIQUID-PHASE IMMUNODIAGNOSTIC ASSAY

[75] Inventor: Roger M. Clemmons, Gainesville, Fla.

[73] Assignee: University of Florida Research Foundation, Inc., Gainesville, Fla.

[21] Appl. No.: 345,283

[22] Filed: Nov. 28, 1994

Related U.S. Application Data

[63] Continuation of Ser. No. 899,222, Jun. 16, 1992, abandoned, which is a continuation of Ser. No. 505,261, Apr. 6, 1990, abandoned.

[51] Int. Cl.$^6$ ................................................. G01N 33/536
[52] U.S. Cl. .................... 435/7.91; 435/7.71; 435/28; 435/188; 436/536
[58] Field of Search ......................... 435/7.71, 7.9, 435/7.91, 17, 18, 25–28, 188, 810, 970, 975; 436/518, 536, 537, 808, 810, 814, 818

[56] References Cited

U.S. PATENT DOCUMENTS

| | | | |
|---|---|---|---|
| 4,062,935 | 12/1977 | Masson et al. | 424/12 X |
| 4,381,921 | 5/1983 | Pierce et al. | 436/535 |
| 4,514,508 | 4/1985 | Hirschfeld | 436/518 |
| 4,536,479 | 8/1985 | Vander-Mallie | 436/537 |
| 4,595,655 | 6/1986 | Self | 435/966 X |
| 4,629,688 | 12/1986 | Bolguslaski et al. | 436/537 X |
| 4,687,735 | 8/1987 | DiNello et al. | 435/25 X |
| 4,783,525 | 11/1988 | McDonald | 530/418 |

FOREIGN PATENT DOCUMENTS

| | | | |
|---|---|---|---|
| 0152254 | 8/1985 | European Pat. Off. | 435/7.71 |
| 0315364 | 5/1989 | European Pat. Off. | 435/7.71 |

OTHER PUBLICATIONS

Raffin, T. et al., "Detection of Immune Complexes by Their Complement-Dependent Binding to Bovine Conglutinin: Technical Aspects of a Solid-Phase Immunoenzyme Microassay and its Application to Normal and Pathological Sera," J. Immunol. Methods 58 (1983) 155–170.

Faaber, P. et al., "Circulating Immune Complexes and Rheumatoid Arthritis: The Induction of Immune Complex Formation Between Rheumatoid Factor and IgG by Polyethylene Glycol," J. Rheumatology 1989; 16:10, pp. 1304–1309.

Lin, T-Y et al., "Interaction of Human C1q with Insoluble Immunoglobulin Aggregates," Immunochemistry, 1978, V. 15, pp. 107–117.

Baumann, Michael, A. and Anderson, Byron, E., "An Immune Complex Selective Affinity Matrix Utilizing a Synthetic Peptide", Oct. 25 1990 issue of The Journal of Biological Chemistry, vol. 266, No. 30, pp. 18414–18422.

*Primary Examiner*—James C. Housel
*Assistant Examiner*—Theresa King
*Attorney, Agent, or Firm*—Saliwanchik, Lloyd & Saliwanchik

[57] ABSTRACT

Reagents for a liquid-phase immunodiagnostic assay (LIDA) method comprise a first enzyme; a second enzyme; a first agent which is capable of binding with an analyte to form a complex, the agent being attached to one of the first and second enzymes; and a complex-binding agent attached to the remaining enzyme, wherein the first enzyme is capable of interacting with a substrate for the first enzyme together with any necessary additional substrates for the first enzyme to produce a substrate for the second enzyme, and wherein the second enzyme is capable of interacting with the substrate produced by the first enzyme together with any necessary additional substrates, such that occurrence of the second of the interactions is detectable. The reagent optionally further comprises a scavenger substance capable of inactivating the substrate produced by the first enzyme.

6 Claims, 4 Drawing Sheets

LEGEND:
A = analyte
Y = first agent
[ = complex-binding agent
Σ = scavenger
E = enzyme
S = substrate
$S^0$ = substrate produced by first enzyme
S' = inactivated substrate
* = detectable signal

LIQUID-PHASE IMMUNODIAGNOSTIC ASSAY

This is a file-wrapper-continuation of prior application Ser. No. 07/899,222, filed Jun. 16, 1992, now abandoned, which was a file-wrapper-continuation of prior application Ser. No. 07/505,261, filed Apr. 6, 1990, now abandoned.

BACKGROUND OF THE INVENTION

The present invention relates to a reagent which is useful in an immunodiagnostic assay method for determining the presence of an analyte in a fluid; to a method for producing the novel reagent; to an immunodiagnostic method using the novel reagent; and to a kit for use in carrying out the assay method.

There are known enzyme immunoassays for determining the presence of an agent in a biologic fluid. One such method is the so-called "EMIT" homogeneous enzyme immunoassay, in which a conjugate is produced comprising an antigen to be assayed and an enzyme. When the conjugate binds to the appropriate antibody, the activity of the enzyme decreases. Conversely, displacement of the conjugate by unbound antigen in the fluid sample results in an increase in enzyme activity which is proportional to the quantity of unbound antigen present. The EMIT procedure requires the use of small haptens, however, and is therefore unsuitable for assaying large molecules.

Pursuant to another method, the homogeneous enzyme-linked immunosorbent assay (ELISA), a solid-phase support, such as a plate, is sensitized by adsorption of antigen thereto. Test antibody in solution is then added, followed by addition of a ligand, which is typically an enzyme linked to a molecule specific for the bound antibody. Finally, a chromogen is added, which generates a colored end-product in the presence of the enzyme portion of the ligand. The optical density of the solution, measured at the end of a defined period, is proportional to the amount of enzyme present and thus to the amount of test antibody.

While the ELISA technique is fairly sensitive, it has the major drawback that it requires the use of solid supports and, consequently, requires washing steps after support sensitization as well as the addition of test antibody and ligand, respectively. All steps must also be performed consecutively. The time required for a typical ELISA is thus approximately 2 to 6 hours. Proper performance of an ELISA requires personnel who are knowledgeable concerning the properties of the assay. In addition, it has proved difficult to modulate the activity of enzyme conjugates of large antigens, such as proteins.

The enzyme immunochanneling assay (EICA) technique employs direct antigen-antibody binding to avoid the problem of modulating enzyme activity. A multienzyme complex is formed in which the product of one enzyme serves as a substrate for the next enzyme. The product can interact with the second enzyme before it escapes to the bulk solution. The first product is thus "channeled" to the second enzyme.

Those EICA methods which require use of solid-phase supports, such as beads or plates, have disadvantages similar to ELISA. While an EICA can be performed without solid supports, moreover, the adaptation of EICA to liquid is a difficult one. In order for the method to operate, the agent to be assayed usually must comprise two epitopes which are relatively close together. This proximity provides the microenvironment necessary for channeling. If a very large molecule has only two useful epitopes, and those epitopes are far apart, it may not be possible to create the required microenvironment. Furthermore, the EICA method requires a separate, specific antibody for each epitope. Since some molecules of potential diagnostic interest lack two distinct useful epitopes, competition between the two antibodies for the same epitope can occur. Under these conditions, it is very difficult to perform the EICA technique.

The channeling binding assay disclosed in U.S. Pat. No. 4,687,735 is carried out in a liquid medium without the use of plates, beads or other conventional solid supports at the start of the assay. But in the disclosed process a linking system is formed which incorporates one of the enzymes of the signal-producing system into a polymeric aggregate, producing a solid support in situ. As in a standard EICA, the analyte must have at least two distinct epitopes.

SUMMARY OF THE INVENTION

Accordingly, it is an object of the present invention to provide a reagent for a true liquid-phase immunodiagnostic assay (LIDA), i.e., an assay that can be carried out wholly in liquid phase, without the need for solid supports or washing steps.

Another object of the present invention is to provide a reagent that does not require a plurality of antibodies or the presence of a plurality of distinct binding sites on the analyte.

A further object of the present invention is to provide a reagent that displays high sensitivity and selectivity.

Still a further object of the present invention is to provide a method for producing such a novel reagent.

Yet another object of the present invention is to provide a liquid-phase immunodiagnostic assay method that employs this inventive reagent.

An additional object of the present invention is to provide a kit for use in carrying out a LIDA method.

In accomplishing the foregoing objectives, there has been provided, in accordance with one aspect of the present invention, a reagent for a liquid-phase immunodiagnostic assay (LIDA) method comprising a first enzyme; a second enzyme; a first agent which is capable of binding with an analyte to form a complex, which agent is attached to one of the first and second enzymes; and a complex-binding agent attached to the remaining enzyme, wherein the first enzyme is capable of interacting with a substrate for the first enzyme, together with any necessary additional substrates for the first enzyme to produce a substrate for the second enzyme, and wherein the second enzyme is capable of interacting with the substrate so produced, again with any necessary additional substrates, such that occurrence of the second of the interactions is detectable. A preferred embodiment of the novel reagent further comprises a scavenger substance capable of inactivating the substrate produced by the first enzyme. The reagent can be in liquid or solid form.

In accordance with another aspect of the present invention, a method for producing the aforementioned reagent is provided that comprises the steps of conjugating one of the first and second enzymes of the reagent to the first agent; conjugating the remaining enzyme to the complex-binding agent by oxidizing the remaining enzyme and subsequently reacting the oxidized enzyme with the complex-binding agent; and combining the two conjugates.

In accordance with still another aspect of the present invention, there is provided an assay method for determining the presence of an analyte in a fluid, in particular a biological fluid, which comprises the steps of providing a reagent as described above which is reactive with the analyte; and combining with the reagent the fluid, a substrate for the first enzyme of the reagent together with any necessary additional substrates for the first enzyme, and any necessary substrates for the second enzyme in addition to the substrate produced by the first reagent.

In accordance with yet another aspect of the present invention there is provided an assay method for determining the presence of an analyte in a fluid, which comprises the steps of providing a solid reagent as described above which is soluble in a liquid present in a sample suspected to contain the analyte and which is reactive with the analyte; and applying the solid reagent to the sample.

In accordance with a further aspect of the present invention, there is provided a kit for use in carrying out a LIDA method which comprises, in packaged combination and in relative amounts to optimize substantially the sensitivity of the assay methods, (a) reagents as described above which are reactive with the desired analyte; (b) solutions comprising substrates for the first and second enzymes of the reagent together with any necessary additional substrates; and (c) means for contacting the reagent with the fluid and the solution.

In accordance with still a further aspect of the present invention, a diagnostic device is provided for carrying out a LIDA method, which device comprises a support, a solid reagent as described above and a membrane permeable, respectively, to the analyte and to the liquid phase carrying the analyte. There is also provided a kit for carrying out the LIDA method using the diagnostic device.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications. Unless otherwise indicated, the respective contents of the documents cited in the following description are hereby incorporated by reference.

BRIEF DESCRIPTION OF THE DRAWING

The invention may be more readily understood by referring to the accompanying drawing by which

DETAILED DESCRIPTION OF PREFERRED EMBODIMENTS

Figure 1A:
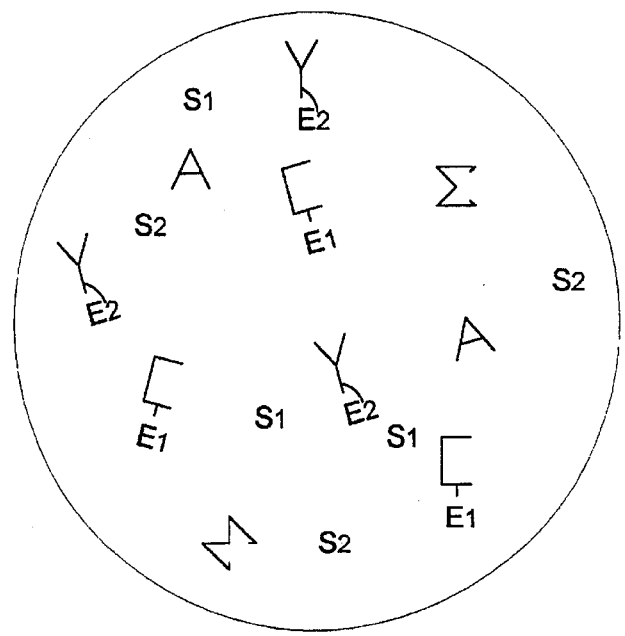
FIGS. 1A–F are schematic representations of the reactions of a LIDA method according to the invention.
Figure 1B:
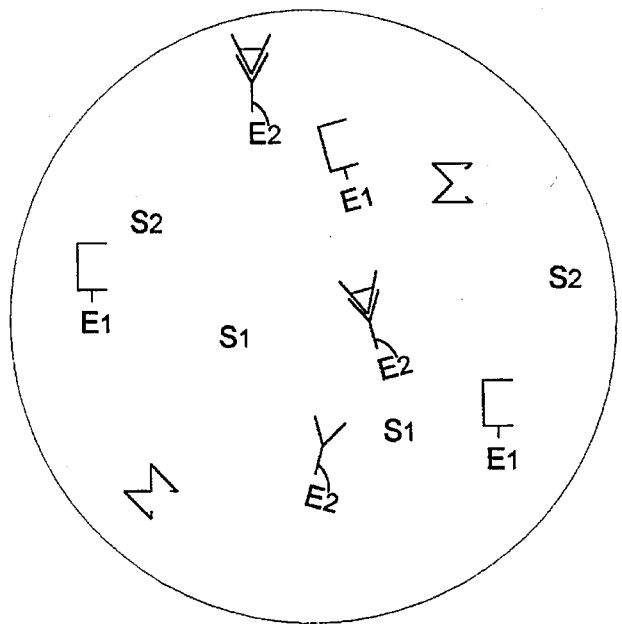
Figure 1C:
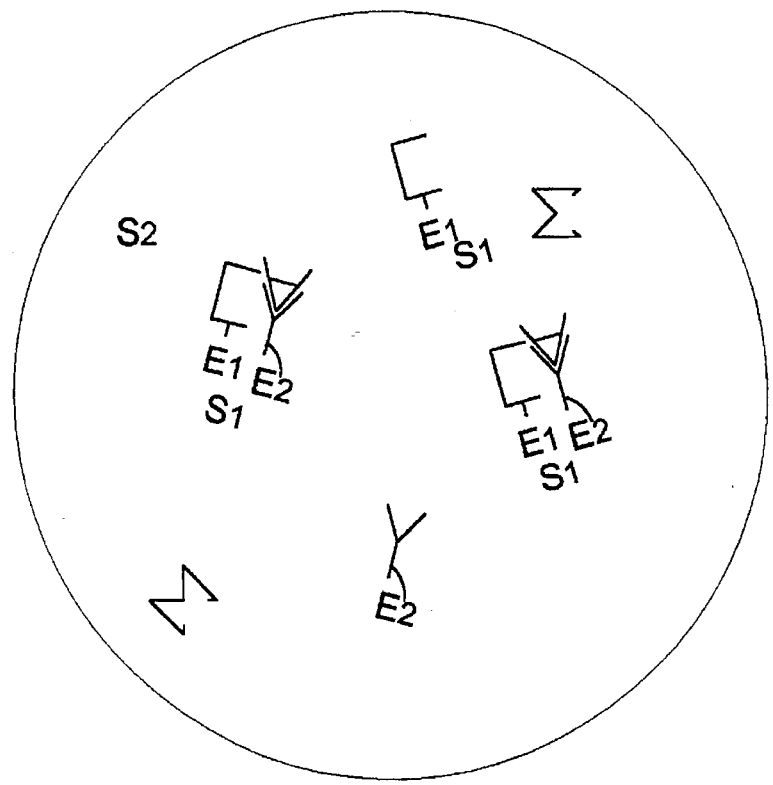
Figure 1D:
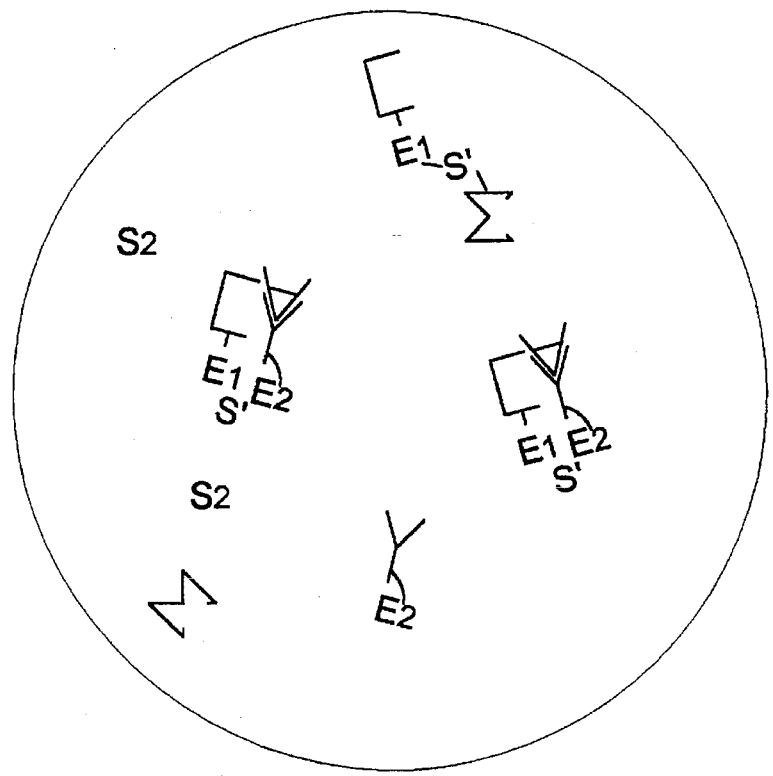
Figure 1E:
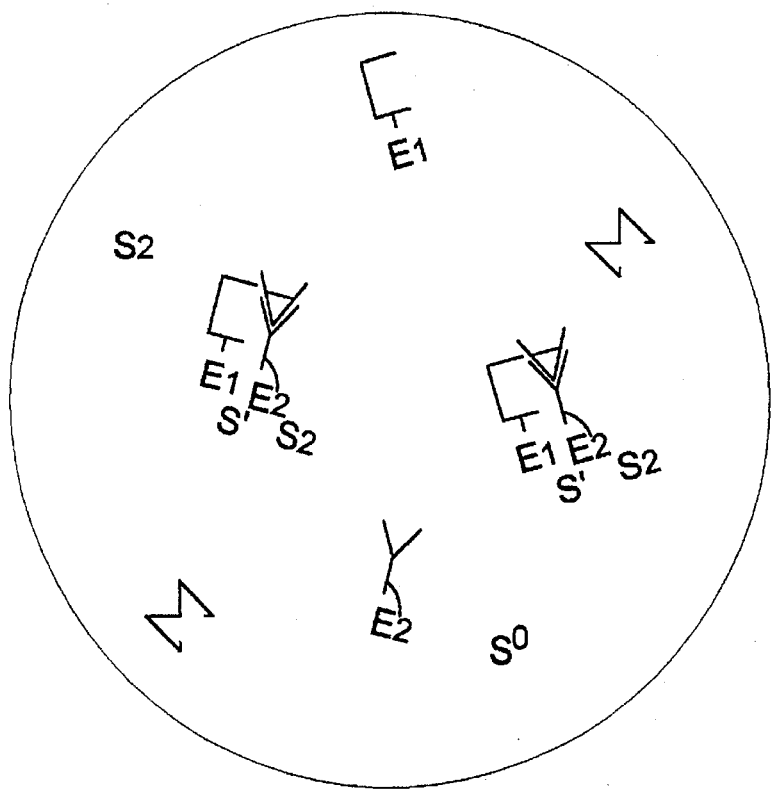
Figure 1F:
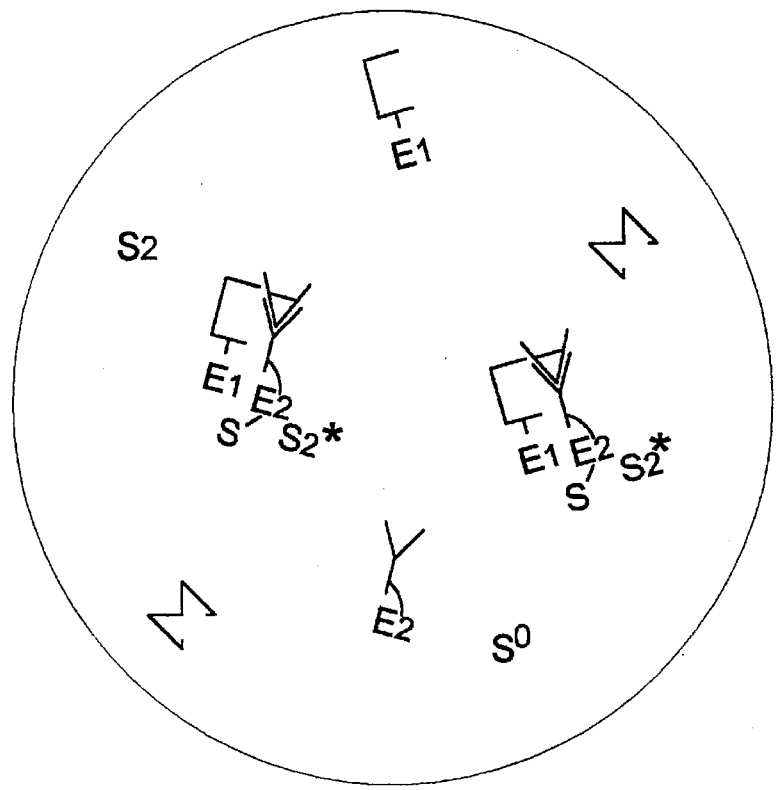

Unless otherwise indicated, the documents cited below are hereby incorporated by reference.

The present invention provides a reagent that is useful in a simplified, rapid technique for determination of the presence in fluids, particularly biological fluids, of a specific analyte, e.g., an antigen or antibody. The complex-binding agent of the reagent, together with the scavenger, mediates a dual-enzyme system which allows specific determination of the presence of the analyte.

The following are definitions of terms used in the description of the reagent according to the invention and in the appended claims:

Analyte—The compound that is the subject of the assay. The analyte can be a small hapten molecule, a large macromolecule, or any other molecule which may be of diagnostic significance. In particular, the analyte can be an antigen, an antibody, a hormone, a drug, an infectious disease vector, a cell-membrane protein fragment, or a receptor, e.g., for IL-1 or nerve-growth factor, which was derived from a cell or which is a soluble receptor from a fragmented cellular matrix.

First Agent—A molecule or compound that forms a complementary binding pair with the analyte. As a function of the specific analyte, the first agent can be, for example, an antibody, an antigen, or a synthetic compound, such as a drug, that is linked to a suitable hapten and thus is capable of eliciting an immune response which results in the formation of a complex.

Antibody—A whole antibody, and antibody fragment. An antibody can be a whole immunoglobulin (IgG) of any class, e.g., IgG, IgM, IgA, IgD, IgE, or a fragment, such as $F(ab')_2$, Fab', Fab and the like. An antibody can further be derived from a non-human source such as mouse, horse, goat or rabbit. An antibody can also be any immunoglobulin or any natural, synthetic or genetically engineered protein that acts like an antibody by binding to a specific antigen to form a complex. The antibody can additionally be an antiidiotypic antibody, in an assay for the particular idiotypic antibody.

Antigen—A molecule that is recognized by the immune system and induces an immune response.

Complex-binding Agent—A molecule or compound that selectively binds to complexes formed by the analyte and the first agent but that does not bind to either one in isolation. The category of suitable complex-binding agents in particular includes all compounds that selectively bind to such complexes due to changes in the conformation of the first agent and/or the analyte upon formation of the complex.

Conjugated LIDA Reagent (CLr)—A compound formed by linking the Complex-binding Agent to one of the first or second enzymes.

Substrate—A substance acted upon by an enzyme. The substrate can be an inorganic molecule such as $H_2O$ or $H_2O_2$, an organic molecule such as glucose or a protein, a molecule such as ATP, etc.

Scavenger—A molecule or compound that is capable of interacting with the substrate produced by the first enzyme to render the substrate incapable of interacting with the second enzyme. Preferably, the scavenger destroys the substrate, for example, by cleavage, oxidization or reduction.

Fluid—Any liquid suspected to contain the analyte. The fluid can be a biological or physiological fluid, such as blood, serum, urine, tears, saliva, sweat, feces or other bodily secretions. The fluid can also be a liquid containing cellular material such as cell lysates, tissue cultures, etc. Additionally, the fluid can be water, a wastewater stream, a manufacturing process stream, and the like.

According to the present invention, the reagent comprises first and second enzymes which constitute a dual enzyme system. The interaction of the first enzyme with a substrate and, if necessary, with one or more additional substrates, produces a molecule or compound which in turn acts as a substrate for the second enzyme. The second enzyme is capable of interacting with the generated substrate in the presence of any necessary additional substrates to produce a detectable output. The output signal may be detected colorimetrically (via measurement of color change by the substrate(s) or of the optical density of the colored solution), electromagnetically (via measurement of photon emission or absorption by the substrate(s)), or in any other desired manner, such as electrochemically, thermally or nephelometrically.

A wide variety of enzymes are useful in coupled enzyme reactions in the context of the reagent according to the present invention. Among the factors to be considered in selecting a dual-enzyme system are enzyme stability, presence of an enzyme or substrate in the fluid sample, sensitivity to chemical modification, fluid pH, ionic strength rate profiles and cost. For instance, a dual-enzyme system comprising a peroxidase is not recommended for use in an assay of an antigen which itself has peroxidase activity. As non-limiting examples of enzyme pairs which are useful in the novel reagent according to the invention, reference is made to the enzyme pairs listed in Tables IV–VII of U.S. Pat. No. 4,275,149.

An illustrative dual-enzyme system which is suitable in the present context is the glucose oxidase/horseradish peroxidase system. The first enzyme, glucose oxidase, interacts with the first substrate, glucose, to generate hydrogen peroxide. Hydrogen peroxide in turn acts as a substrate for horseradish peroxidase, which interacts with a suitable additional peroxidase substrate to produce a color change as the detectable output. Such compounds as ortho-phenylenediamine (OPD), 2,2-azino-di-(3-ethylbenzthiazoline sulfonic acid-6) diammonium salt (ABTS) or 3,3',5,5'-tetramethylbenzidine (TMB) are useful, together with $H_2O_2$, as peroxidase substrates. These and other suitable peroxidase substrates are described in Voller et al., MANUAL OF CLINICAL LABORATORY IMMUNOLOGY, Chapter 17.

Another preferred system is kinase/luciferase, which employs a selected kinase and the corresponding phosphate substrate. In one such system, the first enzyme is creatine kinase, and the substrates are creatine phosphate and ADP. Creatine kinase interacts with the two substrates to produce ATP. The ATP so generated, together with luciferin and $O_2$, in turn serve as substrates for the second enzyme, luciferase. The second interaction generates photons as the detectable signal. Pyruvate kinase can also be used, with phosphoenolpyruvate as the corresponding substrate.

Additional preferred systems include hexokinase/G-6-P dehydrogenase, with phosphofructokinase or phosphoglucose isomerase as the scavenger and NADPH as the detectable signal, and diaphorase/dehydrogenase, with lipoamide dehydrogenase as the scavenger. In the latter system, various dehydrogenases can be employed, together with their corresponding acid anion substrates (e.g., lactic dehydrogenase/lactate). Additionally, various dyes like methyl blue or 2,6-dichlorophenolindophenol can be used as the diaphorase substrate, producing a color change as the detectable signal.

The foregoing reactions are listed in greater detail in Table 1.

The inventive reagent further comprises a first agent which is reactive with the specific analyte whose presence is to be determined. In a preferred embodiment, the first agent and the analyte form a complementary antibody/antigen pair, in which case the first agent can be the antibody or the antigen, depending on whether the corresponding antigen or antibody is the subject of the assay. Preferred antibody/antigen pairs include antibodies to the following antigens: HIV-1 core protein antigens (gag: p17, p18, p24, p55) and envelope proteins (gp41, gp120, gp160); syphilis, gonorrhea, chlamydia and herpes antigens; viral hepatitis antigens; cytomegalovirus antigens; human chorionic gonadotropin; therapeutic drugs such as phenobarbital and digitalis; and drugs of abuse such as cocaine and THC (tetrahydrocannabinol). Additional analytes of potential diagnostic interest are listed in U.S. Pat. No. 4,275,149.

Either the first or the second enzymes of the selected dual-enzyme system can be attached to the first agent of the inventive reagent. Care must be taken in selection of the conjugation method used for joining the first agent to the appropriate enzyme in order to ensure that the resultant enzyme-conjugated first agent is monomeric. Particularly when the first agent is an antibody, the conjugation method employed must be selected such that antibody aggregation is prevented. Should aggregation occur, the complex-binding agent will bind to the aggregates so formed rather than solely to the analyte-first agent complex, thus leading to false positive signal generation. Preferred conjugation methods include the avidin-biotin reaction, and the use of crosslinkers such as SPDP (N-succinimidyl-3-(2-pyridyldithio) propionate) (Pierce). Biotinylated antibodies are particularly useful.

The remaining enzyme is linked to the complex-binding agent, discussed in greater detail below.

Reaction of the first agent and the analyte produces a complex, to which the complex-binding agent of the inventive reagent selectively binds. The compound RhC is a preferred complex-binding agent. RhC is characterized, and methods for its preparation are disclosed, in U.S. Pat. No. 4,783,525. Another complex-binding agent which can be used is the C1q subunit of the first complement component C1. Preparation of C1q is described in U.S. Pat. No. 4,595,654. It is contemplated that any agent that selectively binds to first agent-analyte complexes without binding to either the first agent or the analyte in isolation is suitable for use in the reagent according to the present invention.

The enzyme which is not bound to the first agent is bound to the complex-binding agent to form the conjugated LIDA reagent (CLr). In an exemplary embodiment, the first enzyme is bound to the complex-binding agent, and the second enzyme is bound to the first agent.

Care must be taken in conjugating the complex-binding agent with the selected enzyme to produce the CLr. Preferably the enzyme is oxidized, in particular using the periodate method, and subsequently linked to the complex-binding agent. Such treatment of the enzyme, rather than the complex-binding agent, is especially preferred when the complex-binding agent is RhC, as it has been found that treatment of RhC in certain media, such as strongly ionic buffers, destroys its activity. While the reason for this loss of activity is not known with certainty, it is believed that RhC is an ionic dimer, and as such is susceptible to structural disruption and loss of functional groups upon treatment with ionic buffers. This problem does not arise when the enzyme, rather than the complex-binding agent, is treated.

The CLr can also be produced by conjugation of the enzyme and the complex-binding agent using the one-step glutaraldehyde method. This method may be preferable in certain circumstances, but the efficiency of the method is low.

The inventive reagent can be used with or without a scavenger. The choice of a reagent either comprising or excluding a scavenger will depend on circumstances such as the conditions under which the assay is to be carried out, availability of specific enzymes, cost, time constraints, etc.

Both of the foregoing embodiments of the novel reagent and assay, i.e., embodiments with or without a scavenger, exploit the concept of bulk fluid compartmentalization. In regions of the solution in which no analyte is present (and, by the same token, in a sample which is free from the analyte), no analyte-first agent complex forms. Since there are no complexes in the solution, the CLr does not bind, and consequently the first and second enzymes are not brought into close proximity. Under these conditions, in the presence of the necessary substrates for the two enzymes, the conjugated first enzyme reacts to produce a substrate required by the second enzyme. This substrate subsequently diffuses to the second enzyme, which then generates the output signal. Signal generation occurs at a rate characterized by rate constant $k_1$.

In regions where the analyte is present, on the other hand, it rapidly forms a complex with the first agent. Virtually immediately upon formation of the complex, the CLr binds thereto. The first and second enzymes are thus placed in close contact. In the presence of the necessary substrates, the first enzyme then generates a substrate for the second enzyme, as described previously. This substrate is channeled to the second enzyme, which then produces the output signal. Signal generation in this case occurs at a rate characterized by the higher rate constant $k_2$.

Use of the novel reagent without a scavenger in a LIDA method according to the invention exploits the difference in the kinetic response of the two-enzyme system depending on the proximity of the two enzymes to each other, i.e. the difference between $k_1$ and $k_2$. The observed rate constant for the production of the detectable output in this embodiment is $$K_3 = (1-x)k_1 + xk_2,$$

where x is the fraction of enzyme pairs which are in close contact. The fraction of enzymes in close contact is equal to the ratio of the concentration of analyte in the fluid sample to the concentration of the first agent (assuming that the former does not exceed the latter). As a result, $x = n_A/n_{FA}$, where $n_i$ denotes moles of analyte and first agent for i=A and FA, respectively. The observed rate constant then becomes $k_3 = k_1 + [n_A/n_{FA}](k_2 - k_1)$. This observed rate constant is proportional to $n_A$. Thus, with $k_1$, $k_2$ and $n_{FA}$ known, measurement of $k_3$ gives $n_A$. It must be noted that this result is only valid when $k_1$ is non-zero, and $k_1$ and $k_2$ are distinguishable from each other and also from $k_3$.

When the novel reagent is used with a scavenger in a LIDA method according to the invention, on the other hand, the scavenger inactivates the substrate generated by the first enzyme before it can reach the second enzyme. This embodiment thus suppresses any output of a detectable signal unless the first and second enzymes are in close proximity to one another. In other words, the rate constant $k_1$ in the preceding analysis is zero when the scavenger is used. But when the analyte is present, complex formation and subsequent CLr binding occurs, and the first and second enzymes are brought into close proximity. In the presence of the necessary substrates, the first enzyme then produces the substrate required by the second enzyme, as described above.

The compound so produced by the first enzyme is channeled to the second enzyme before the scavenger can inactivate it. The second enzyme then generates the detectable output. Measurement of the output signal strength allows determination of the amount of the analyte. The amount of enzyme activity in this embodiment is directly proportional to the amount of analyte within the sample. Through preparation of standard assay media having known concentrations of the analyte, one can calibrate the output signal strength to the analyte concentration. Once the calibration is established, the observed signal allows determination of the concentration of the analyte.

The advantage of preparing the reagent according to the present invention without a scavenger lies in the greater range of enzyme pairs which can used therein. There may be no readily available or economical scavenger for use with certain potentially desirable enzyme pairs. Also, since only two enzymes are used, there is no need to optimize the compatibility of three separate compounds in the inventive reagent. This embodiment is especially useful if the difference between $k_2$ and $k_1$ is large. Preferably, the sample containing the analyte is combined with the reagent, and the substrates are added after a sufficient incubation period. If the substrate for the first enzyme is present before the analyte is added, the first enzyme can interact with and potentially deplete the substrate. It is also necessary to ascertain that the sample itself does not contain substrates for the selected enzymes.

The advantage of preparing the inventive reagent with a scavenger lies in overall simplification of the assay method. When a scavenger is used, the sample, reagent and substrate solution can be combined at the same time—no incubation step is needed, and substrate depletion is not a problem. It is also unnecessary to ensure that the sample solution is free of substrates for the first and second enzymes. This embodiment also avoids the problem of inaccurate determination of $n_A$ when $k_1$ and $k_2$ are of comparable magnitude. Finally, use of the scavenger ensures that the strength of the signal is proportional to the amount of analyte present in the solution.

Exemplary of the latter preferred embodiment are those systems which can use catalase as a scavenger, such as the above-described glucose oxidase/horseradish peroxidase system. Catalase inactivates the hydrogen peroxide substrate, generated by glucose oxidase, by converting it to water. Other enzymes which destroy hydrogen peroxide are also suitable for use with this enzyme system.

The novel reagent can be provided in either a liquid or a solid form. In the former embodiment, the reagent further comprises a liquid, preferably aqueous, carrier for the reagent constituents. One or more co-solvents can also be used. The first agent, CLr, and substrates for the first and second enzymes, along with the scavenger, if used, can be combined in the same solution or in two or more separate solutions. The temperature of the solution(s) is preferably in the range of about 20 to 56° C., and the pH thereof is preferably from about 7.1 to 8.4. Adjustment of the concentrations of the reagent components in the solution(s) in order to optimize sensitivity is within the skill of the ordinary artisan.

The novel reagent can also be provided in a solid form. In a preferred embodiment, the first agent, CLr and optional scavenger are stabilized, e.g., with sucrose, and then lyophilized. The various components of the inventive reagent can be lyophilized separately or in any desired combination. Before performance of the assay according to the invention, the components of the lyophilized reagent are reconstituted in a suitable liquid carrier.

In another embodiment, the reagent, optionally together with appropriate substrates, is provided in solid form for use in another embodiment of the LIDA method (the "solid LIDA method") which is described below. The solid reagent, or reagent/substrate combination, can be dispersed within a wettable matrix, e.g., by soaking the matrix material in a solution of the reagent and optionally one or more substrates and then drying. Preferably, the solution does not include all necessary substrates for both enzymes, in order to prevent reaction during the manufacture of the solid form of the reagent. Particularly preferably, the substrate for the first enzyme (or one of said substrates if more than one is required) is omitted from the solid form of the reagent. For certain enzymes in certain applications, the omitted substrate is present in the fluid sample, and therefore need not be added. For example, glucose oxidase can be used in the solid form of the inventive reagent; when blood or urine is the fluid to be assayed, the glucose already present therein serves as the necessary substrate. In other applications, the omitted substrate(s) must be added to the sample.

The matrix can comprise wettable components such as cotton, wool or glass fibers, and is preferably enclosed in an inert, porous membrane which admits fluids and desired analytes but excludes cellular debris, etc. Suitable membranes include nylon, polypropylene and polycarbonate. In this embodiment the reagent preferably comprises a scavenger.

In an embodiment of the LIDA method according to the present invention, a sample solution comprising the fluid suspected to contain the analyte is added to a solution comprising the reagent—first agent, CLr and, optionally, a scavenger—together with the appropriate substrates for the first and second enzymes. Signal production indicates the presence of the analyte. In another embodiment of the LIDA method, the sample solution is first added to the reagent. The substrates are then added to the combined reagent/sample following an incubation step. In another preferred embodiment, each of the fluid sample and the substrates for the first and second enzymes are added to the reagent sequentially. In yet another preferred embodiment, the fluid, substrates and optional scavenger are combined, and the resulting mixture is added to the reagent; in this case the reagent does not comprise the scavenger. Other combinations are also possible and are contemplated to be within the scope of the present invention.

In the solid LIDA method according to the invention, the solid form of the reagent is introduced into the sample to be assayed, e.g., blood, urine or feces. The sample must comprise a liquid phase, and the selected solid reagent matrix material must be wettable by this liquid. If necessary, one or more substrates are added to the sample. When the liquid phase present in the sample interacts with the reagent (i.e., dissolves the dried reagent), reaction occurs in the resultant solution as in the foregoing embodiments. A preferred detectable output in the solid LIDA method is a color change. The signal can be interpreted qualitatively (color change indicates presence of analyte) or quantitatively (e.g., measurement of reflectance indicates amount of analyte).

The LIDA method allows rapid, quantitative assay of numerous biological fluids for the presence of a wide range of agents. Concentrations of analyte are detectable in concentrations as low as $10^{-12}$ to $10^{-15}$ g/l by use of the inventive LIDA method. Concentrations greater than about $10^{-3}$ g/l preferably are diluted prior to assay.

The method is particularly suited for automation. A LIDA can be carried out using most clinical analyzers which currently run EMIT tests, such as the Encore II System Special Chemistry Analyzer (product of Serono-Baker Diagnostics Corporation). The method can also be carried out using spectrophotometric systems, including the Baker 1.2.3. Chemistry Analyzer. The solid LIDA method can be carried out using an analyzer, such as the Boehringer Mannheim Reflotron, to measure reflectance.

For convenience, the reagent of the present invention can be provided as a kit, with all constituents in predetermined proportions so as to substantially optimize the sensitivity of the assay in the range of interest. Preferably the reagent is provided in a liquid carrier, but the components of the reagent can also be provided in lyophilized form to be reconstituted in an appropriate liquid carrier by the user. The kit also comprises a solution of the necessary substrates for the selected dual enzyme system, or lyophilized substrates which are reconstituted prior to assay, and means for contacting the reagent with the biological fluid sample and the substrate solution. Such means include, for example, disposable containers, vials, syringes, etc. The solid LIDA reagent can be provided in the form of a diagnostic device such as a dipstick. The solid LIDA reagent can be accompanied in a kit by the necessary additional substrates, which can be in liquid or solid (e.g., lyophilized) form.

For reagents which do not use a scavenger, the quantities of the various components of the inventive reagents should be such as to provide a reaction rate on detection of the analyte which is at least two times that of the reagent blank, i.e., a zero sample.

The LIDA method according to the invention is useful for detection of a wide range of analytes. Exemplary diagnostic uses of the inventive method include: monitoring the state of infection of a disease, such as AIDS (e.g., by monitoring the levels of HIV antigens, IgM and IgG over time) or hepatitis B; evaluating the therapeutic effect of drugs; determining the presence of drugs of abuse; and establishing the presence of human chorionic gonadotropin (indicative of pregnancy).

With reference to the drawings, FIGS. 1A–F illustrate an exemplary embodiment of the inventive assay using a scavenger, in which a reagent according to the invention, the substrates for the first and second enzymes, and the fluid sample containing the analyte are combined. The first enzyme is attached to the complex-binding agent, and produces a substrate for the second enzyme, which is attached to the first agent. The reaction producing the detectable output occurs when this second enzyme interacts with a substrate in the presence of the substrate generated by the first enzyme.

Figure 2:
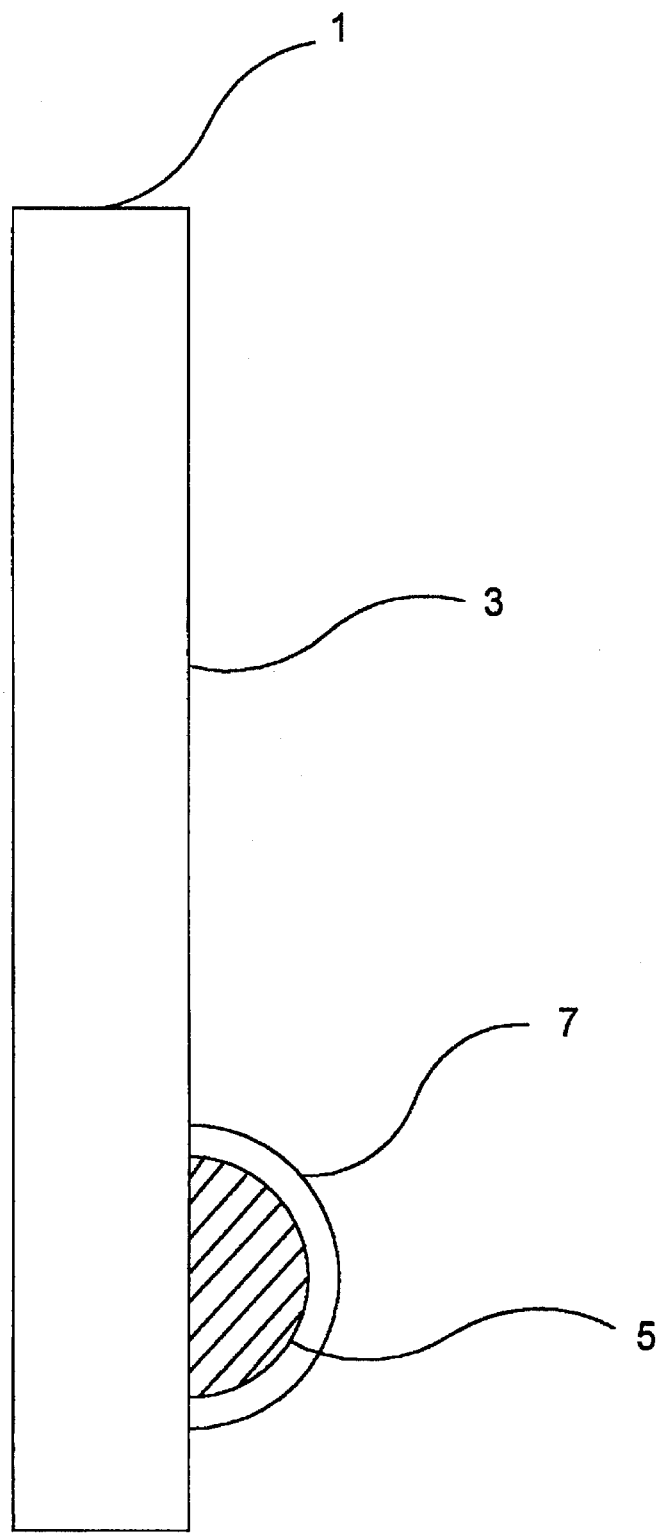
FIG. 2 is a sectional view of a diagnostic device according to the invention.

FIG. 2 illustrates in sectional view a diagnostic device according to the invention. The diagnostic device 1, in the form of a dipstick, comprises a plastic backing strip 3, to which is attached a solid LIDA reagent 5 comprising a wettable matrix, e.g., of cotton, wool or glass fibers, in which is dispersed the components of the selected LIDA reagent and optionally one or more enzyme substrates. Reagent 5 is enclosed between backing strip 3 and membrane 7, which is also attached to backing strip 3. In use, the dipstick 1 is inserted into the sample so that reagent 5 and membrane 7 are immersed therein. The liquid present in the sample penetrates membrane 7 and wets reagent 5, which causes the components of the LIDA reagent and any substrates dispersed therein to dissolve. If necessary, necessary additional substrates are added to the sample. The enzymatic reactions of the LIDA method then take place if the assayed analyte is present.

Illustrative embodiments of the invention are given below.

Preparation Example

CLr comprising RhC conjugated to a selected enzyme is prepared according to the following protocols:

(1) Periodate conjugation
  (a) AP-RhC conjugation

Alkaline phosphatase (AP), 0.38 ml, 12.1 mg/ml (Type VIII-T, 12.1 mg/ml; 13,158 units/ml, Sigma P-6774) is dialyzed in 4×100 μl aliquots against 4×100 ml changes of 0.1M sodium acetate buffer, pH 4.0, for 1 hour at room temperature. Sodium metaperiodate, 19 μl, 0.4M is then added with gentle stirring. The solution is incubated 30 minutes at room temperature in the dark. The oxidized AP is dialyzed in 4×100 μl aliquots against 3×100 ml changes of 10 mM sodium acetate buffer, pH 4.0, in the dark for 1 hour at room temperature.

RhC, 0.25 ml, 20 mg/ml (McDonald, U. of Nebraska) is dialyzed in 2×125 μl aliquots against 3×100 ml changes of 0.1M sodium borate buffer, 0.1M NaCl, pH 9.0 for 1 hour at room temperature. The RhC and the oxidized AP are then combined with gentle stirring at 4° C., then incubated overnight in the dark at 4° C.

Sodium borohydride, 2.5 mg, is then added at 4° C. with stirring, followed by incubation for 4 hours at 4° C. The product is dialyzed against 3×100 ml changes of 10 mM Tris/HCl, pH 8.0 overnight at 4° C. The precipitate is separated at 15,000×g for 15 minutes, washed with 3×0.5 ml cold 10 mM Tris/HCl, pH 8.0, and finally dissolved with 0.5 ml, 0.25M Tris/HCl, 0.5M NaCl, pH 8.0 and stored at 4° C.

(b) GO-RhC conjugation

Glucose oxidase (GO), 2 ml, 5.3 mg/ml (Type V-S, 5.3 mg/ml; 1130 units/ml, Sigma G-6891) is concentrated to 1.2 ml using a Centriflo CF-25 ultrafiltration cone (Amicon). The GO is dialyzed in 5×240 μl aliquots against 4×100 ml changes of diH$_2$O. Then 0.3 ml, 0.1M freshly prepared sodium meta-periodate in 10 mM sodium phosphate buffer, pH 7.0 is added. The solution is incubated 20 min. at room temperature. The oxidized GO is then dialyzed in 5×300 μl aliquots against 4×100 ml changes of 1 mM sodium acetate, pH 4.0 for 2 hours at room temperature.

RhC (0.25 ml, 20 mg/ml) is dialyzed in 2×125 μl aliquots against 4×100 ml changes of 20 mM borate buffer, 0.5M NaCl, pH 9.0 for 2 hours at room temperature. The RhC and oxidized GO are combined and incubated 2 hours at room temperature. The Schiff bases are then reduced by adding 100 μl sodium borohydride, 4 mg/ml, prepared fresh with deionized H$_2$O. The solution is incubated for 2 hours at 4° C. The product is then dialyzed in 5×350 μl aliquots with 4×100 ml changes of 10 mM Tris/HCl, 0.25M NaCl, pH 8.0.

(c) HRP-RhC conjugation

Horseradish peroxidase (HRP), 5 mg (Type VI, RZ 3.0, Sigma P8375) is dissolved in 1.2 ml diH$_2$O. Freshly prepared sodium meta-periodate, 0.3 ml, 0.1M in 10 mM sodium phosphate, pH 7.0, is added. The solution is incubated 20 min. at room temperature. The oxidized HRP is dialyzed in 5×300 μl aliquots 4×100 ml changes of 1 mM sodium acetate, pH 4.0 in a microdialyzer (Pierce, Series 500 Microdialyzer) for 2 hrs at room temperature.

RhC (0.25 ml, 20 mg/ml) is dialyzed in 2×125 μl aliquots against 4×100 ml changes of 20 mM borate buffer, 0.5M NaCl, pH 9.0 for 2 hrs at room temperature. The RhC and oxidized HRP are combined and incubated 2 hrs at room temperature. The Schiff bases are then reduced by adding 100 μl, 4 mg/ml sodium borohydride freshly prepared with diH$_2$O. The solution is incubated 2 hrs at 4° C. The product is then dialyzed in 5×350 μl aliquots against 4×100 ml changes of 10 mM Tris/HCl, 0.25M NaCl, pH 8.0 overnight at 4° C.

(2) Glutaraldehyde conjugation
  (a) GO-RhC conjugation (first method)

RhC (0.25 ml, 20 mg/ml) is dialyzed in 2×125 μl aliquots against 4×100 ml changes of 50 mM potassium phosphate buffer, 0.5M NaCl, pH 7.2 for 2 hrs at room temperature in a microdialyzer (Pierce, Series 500 Microdialyzer).

Glucose oxidase, 1.26 ml, 5.3 mg/ml (Type V-S, 5.3 mg/ml; 1130 U/ml, Sigma g-6891) is dialyzed in 5×250 μl aliquots against 4×100 ml changes of 50 mM potassium phosphate buffer, 0.5M NaCl, pH 7.2 for 2 hrs at room temperature in a microdialyzer. To the GO are added 0.29 ml 50 mM potassium phosphate buffer, 0.5M NaCl, pH 7.2, and 10 μl, 25% glutaraldehyde (glutaraldehyde, 50%, EM grade, Ted Pella, Inc. 18432) with stirring. The mixture is incubated 50 min at room temperature.

The RhC and the GO/glutaraldehyde solution are combined and incubated 75 min at room temperature. The mixture is then cooled to 0° C. in an ice bath. Then 100 μl 2M Tris/HCl, pH 8.7 are added and the mixture is stirred 30 min at 4° C. Sodium borohydride, 30 mg/ml is prepared fresh in ice cold diH$_2$O and 100 μl thereof is added at 0° C. The mixture is incubated 2.5 hrs at 0° C. Finally, the product is dialyzed in 5×400 μl aliquots against 4×100 ml changes of 10 mM Tris/HCl, 0.25M NaCl, pH 8.0 overnight at 4° C.

(b) GO-RhC conjugation (second method)

Glucose oxidase, 1 ml, 5.3 mg/ml (Type V-S, 5.3 mg/ml; 1130 units/ml, Sigma G-6891) is dialyzed in 5×200 μl aliquots against 3×100 ml changes of 0.1M sodium phosphate buffer, pH 6.8 for 2 hrs at room temperature in a microdialyzer (Pierce, Series 500 Microdialyzer).

RhC (1 ml, 5.3 mg/ml) is dialyzed in 5×200 μl aliquots against 3×100 ml changes of 10 mM Tris/HCl, pH 8.0 for 2 hrs at room temperature. The precipitate is separated at 15,000×g for 15 sec. The pellet is then redissolved in 1 ml GO in 0.1M sodium phosphate buffer, pH 6.8 in a 5 ml beaker with micro-magnetic stir bar. With gentle stirring, 0.15 ml, 1% glutaraldehyde (25% glutaraldehyde, Sigma G-6257, not EM grade) is added. The solution is incubated 2 hrs at room temperature. The product is then dialyzed in 5×200 μl aliquots against 3×100 ml, 0.01M PBS (phosphate buffered saline), pH 7.4 overnight at 4° C. Any flocculent material is removed at 15,000×g for 30 min. The supernate is stored at 4° C.

CLr comprising C1q rather than RhC can be prepared in a similar manner.

The first agent (e.g. HRP-Ab, GO-Ab) is then prepared by conjugating, e.g., HRP or GO with the selected antibody (for example, antibody to HIV p24 antigen), using an appropriate method, such as the avidin-biotin method.

The CLr and enzyme-conjugated first agent are then purified using liquid chromatography on a 10–100 cm column (O.D. 0.5–1.5", Pharmacia). The column is packed with SEPHAROSE® (a size-exclusion chromatography gel) 6 B for CLr or antibody (first agent) separations. The elution buffer is 10 mM Tris in 0.25M NaCl at pH 8.0. The flow rate is set at 1 ml/min. The peaks are monitored as the fluid passes a flow cell, at 280 nM. The peaks are collected with a fraction collector and all fractions that correspond to the first peak are pooled to represent the conjugated material. Subsequent peaks, including unconjugated enzyme and antibody or complex-binding agent, are monitored and discarded.

The enzyme activity is then tested. A protein determination is made on the purified first agent or CLr using a micro-protein method (Micro BCA assay reagent kit, Pierce) and an Encore II Special Chemistry System (Serono-Baker Diagnostics), and the enzyme activity is measured using standard methods (Sigma Chemical Company) to establish the specific activities of the enzymes/mg of protein.

Use Example 1

A phosphate buffer (PB) solution is prepared as a liquid carrier. PBS is mixed with 3% polyethylene glycol 6000, 0.05% TWEEN® (polyoxyethlenesorbitan monolaurate, a surfactant) 20, and 0.1% ovalbumin.

A PBS solution is prepared as a second liquid carrier. To 27 mM P+0.41M NaCl is added 8.2% polyethylene glycol 6000, 0.14% Tween 20 and 0.27% ovalbumin. This produces a 10 mM PBS solution.

A first solution comprising the reagent is prepared by combining 190 µl of PBS solution, 100.0 µl HRP-avidin-biotin-Ab (0.278 mg/ml) and 10.0 µl GO-RhC CLr. This is sufficient to provide 300 µl of the reagent solution.

A second solution comprising substrates and scavenger is prepared by combining 10 mM ABTS, 250 mM glucose and 10.0 µl/ml catalase in the PB solution. A 2.5 ml quantity is sufficient for the 300 µl volume of the first solution. Use of the foregoing PB solution assists in forming a precipitate and enhances the reaction, but formation of a precipitate is not necessary for carrying out the assay.

The following fluid volumes are specified:
a) sample volume=3 µl
b) diluent volume ($H_2O$)=10 µl
c) first solution volume=30 µl
d) second solution volume=210 µl The assay is carried out using the Encore System II (Encore P2000 pipetter/Encore Analyzer). The Encore P2000 pipetter automatically pipettes the sample or standard (with diluent) and second solution into the sample well, and the first solution into the reagent well. The transfer disk is then placed into the Encore II. The sample/second solution mixture and the first solution are combined and sent to the cuvette at the initiation of the spin cycle. After an initial blanking period, the optical density of the reaction mixture is monitored over time at 405 nM, and the result is compared to a generated standard curve to read the concentration of analyte in the sample.

Use Example 2

The sample, diluent and second solutions are as in Use Example 1.

A first solution comprising the reagent is prepared by combining 396.0 µg/ml HRP-avidin-biotin-Ab, 180.0 µg/ml GO-RhC CLr, 0.05% Tween 20 and 1% ovalbumin in PBS solution.

The following fluid volumes are specified:
a) sample volume=3 µl
b) diluent volume ($H_2O$)=10 µl
c) first solution volume=20 µl
d) second solution volume=210 µl The sample is analyzed in the Encore System II in the same manner as in Use Example 1.

In each of the preceding Use Examples, the RhC-enzyme CLr can be replaced by C1q-HRP or C1q-GO, as appropriate.

TABLE 1

| | REACTION | |
|---|---|---|
| 1) Glucose | —Glucose Oxidase→ | $H_2O_2$ + Gluconate |
| $H_2O_2$ + ABTS | —Horseradish Peroxidase→ | Colored Product |
| 2) Creatine Phosphate | —Creatine Kinase→ | ATP + Creatine |
| Luciferin + ATP + $O_2$ | —Luciferase→ | Luciferin = O + AMP + PPi + $CO_2$ + hv |
| 3) Glucose + ATP | —Hexokinase→ | Glucose-6-Phosphate + ADP |
| G-6-P + NADP | —G-6-P Dehydrogenase→ | Gluconolactone-6-P + NADPH |
| 4) NAD + Lactate | —Lactic Dehydrogenase→ | NADH + Pyruvate |
| Thiazolyl Blue = O + NADH | —Diaphroase→ | Thiazolyl Blue = $H_2$ + NAD |

| ENZYME 1 | SUBSTRATE(S) 1 | SCAVENGER | ENZYME 2 | SUBSTRATE 2 | OUTPUT |
|---|---|---|---|---|---|
| 1. Glucose Oxidase | Glucose | Catalase | Horseradish Peroxidase | ABTS, $H_2O_3$ | (Colored Product) |
| 2. Creatine Kinase | Creatine Phosphate, ADP | ATP-ase | Luciferase | Luciferin, ATP, $O_2$ | hv |
| 3. Hexokinase | Glucose, ATP | Phosphofructokinase, Phosphoglucoseisomerase | G-6-P Dehydrogenase | G-6-P, NADP | NADPH |
| 4. Lactic Dehydrogenase | Lactate, NAD | Lipoamide dehydrogenase | Diaphorase | NADH, Thiazolyl Blue = O | Thiazolyl Blue = $H_2$ |

What is claimed is:

1. An assay method for determining the presence of an analyte in a fluid, which method is carried out wholly in liquid phase without the need for a solid support, and comprises the steps of:
   (a) providing a reagent mixture comprising
      (i) a first enzyme;
      (ii) a second enzyme;
      (iii) an agent which specifically binds said analyte to form an immune complex, said agent being conjugated to one of said first and second enzymes such that said conjugate is monomeric; and
      (iv) an immune complex-binding agent which selectively binds to in said immune complex, but not analyte or agent alone, said immune complex-binding agent being conjugated to the remaining enzyme, wherein said agent and said immune complex-binding agent are not bound to a solid phase carrier or polymerized into an aggregate complex;
   (b) combining with said reagent mixture said fluid, a substrate with which said first enzyme interacts to produce a product that is a substrate for said second enzyme, wherein said second enzyme interacts with said product to produce a detectable output signal within said fluid;
   (c) detecting said output signal within said fluid produced in step (b); and
   (d) determining the presence of said analyte in said fluid.

2. The assay method as claimed in claim 1, wherein said fluid is added to said reagent mixture, and subsequently a solution comprising said substrate is added to the combined reagent mixture/fluid.

3. The assay method as claimed in claim 1, wherein said fluid is added to sad reagent mixture, and subsequently a solution comprising said substrate and a scavenger substance capable of inactivating said product are added to the combined reagent mixture/fluid.

4. The assay method as claimed in claim 3, wherein said fluid and separate solutions (i) comprising said scavenger substance and (ii) comprising said substrate are sequentially added to said reagent mixture/fluid.

5. The assay method as claimed in claim 1, wherein said reagent mixture further comprise a scavenger substance capable of inactivating said product.

6. An assay method for determining the presence of an analyte in a fluid, which method is carried out wholly in liquid phase without the need for a solid support, and comprises the steps of
   (a) providing an analytical device comprising a support, a porous membrane and a reagent mixture comprising
      (i) a first enzyme;
      (ii) a second enzyme;
      (iii) an agent which specifically binds said analyte to form an immune complex, said agent being conjugated to one of said first and second enzymes such that said conjugate is monomeric; and
      (iv) an immune complex-binding agent which selectively binds to in said immune complex, but not analyte or agent alone, said immune complex-binding agent being conjugated to the remaining enzyme, wherein said agent and said immune complex-binding agent are not bound to a solid phase carrier or polymerized into an aggregate complex and wherein said reagent mixture is dispersed in a dry state within a wettable solid matrix, said reagent mixture being disposed between said support and said membrane;
   (b) applying said analytical device to said fluid, whereby said fluid wets the wettable matrix of said analytical device;
   (c) detecting said output signal within said fluid produced in step (b) within said fluid within said wettable matrix; and
   (d) determining the presence of said analyte in said fluid.

* * * * *

UNITED STATES PATENT AND TRADEMARK OFFICE
CERTIFICATE OF CORRECTION

PATENT NO. : 5,637,473

DATED : June 10, 1997

INVENTOR(S) : Roger M. Clemmons

It is certified that error appears in the above-identified patent and that said Letters Patent is hereby corrected as shown below:

Column 13, line 23: "10.0 ul/ml" should read --10.0 µg/ml--.

Column 15, line 14: "binds to in said" should read --binds to said--;

line 35: "sad" should read --said--.

Column 16, line 6: "comprise" should read --comprises--;

Column 16, line 20: "to in said" should read --to said--.

Signed and Sealed this

Ninth Day of December, 1997

Attest:

BRUCE LEHMAN

Attesting Officer

Commissioner of Patents and Trademarks